Figure 4:
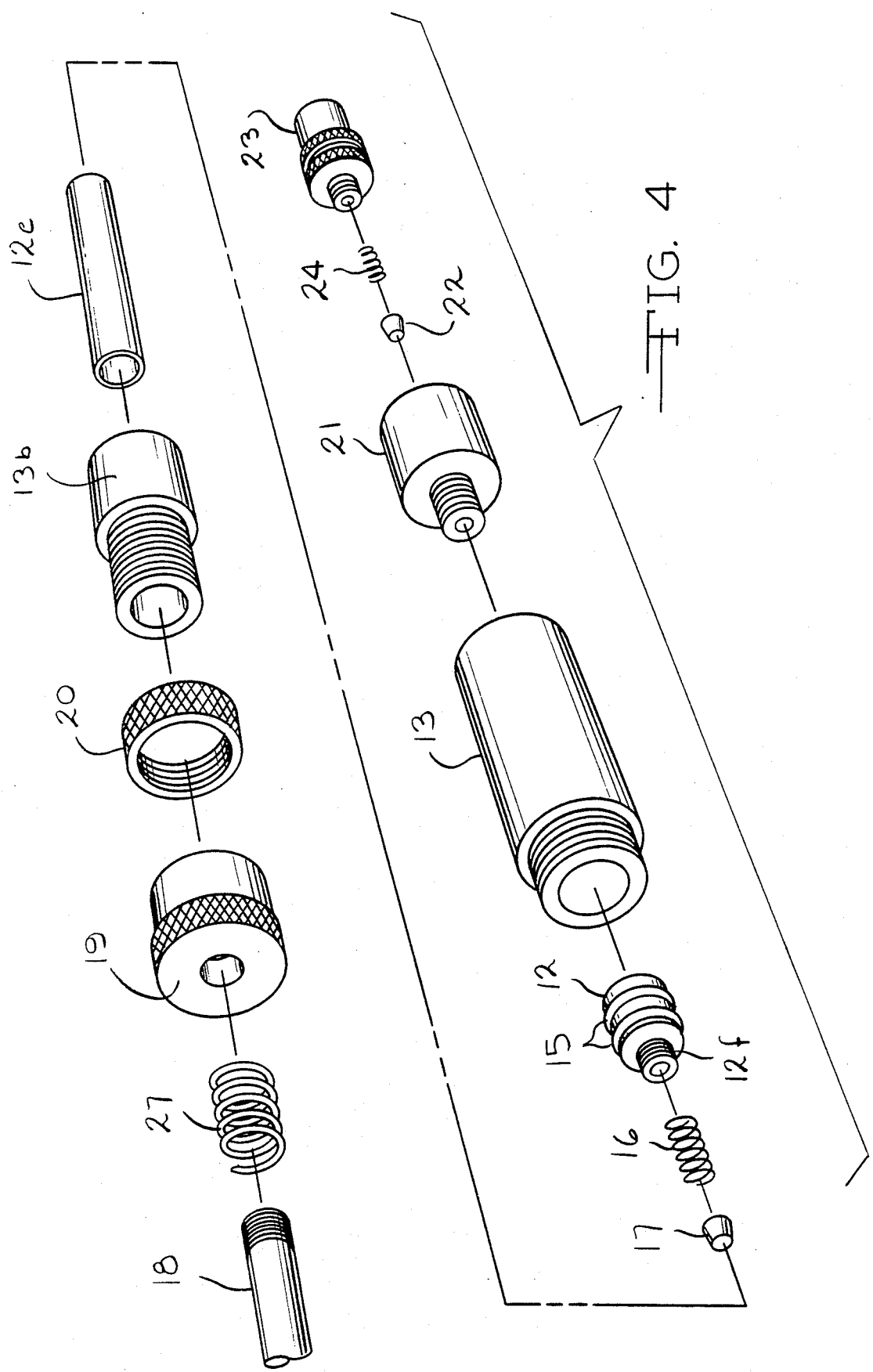

United States Patent [19]

Prindle

[11] Patent Number: 4,747,834
[45] Date of Patent: May 31, 1988

[54] BACK-FILL SYRINGE

[75] Inventor: Gordon E. Prindle, Schaumburg, Ill.

[73] Assignee: Ideal Instruments, Inc., Chicago, Ill.

[21] Appl. No.: 101,431

[22] Filed: Sep. 28, 1987

Related U.S. Application Data

[63] Continuation-in-part of Ser. No. 909,481, Sep. 19, 1986, Pat. No. 4,715,853.

[51] Int. Cl.$^4$ ............................................. A61M 5/18
[52] U.S. Cl. .................................. 604/184; 604/247; 141/2; 141/27; 141/383
[58] Field of Search ............... 604/181, 183, 184, 247, 604/255–257, 403, 407, 411; 141/2, 19, 27, 329, 330, 383

[56] References Cited

U.S. PATENT DOCUMENTS

| | | | |
|---|---|---|---|
| 1,995,971 | 3/1935 | Dowling | 604/183 |
| 2,374,368 | 4/1945 | Mejia | 604/183 |
| 2,538,391 | 1/1951 | Smith | 604/184 |
| 2,645,224 | 7/1953 | Beebe | 604/183 |
| 2,757,670 | 8/1956 | Ogle | 604/407 |
| 2,821,193 | 1/1958 | Ziherl et al. | 604/71 |
| 2,821,195 | 1/1958 | McLintock | 604/184 |
| 3,343,539 | 9/1967 | Moorhouse | 141/27 X |
| 3,353,537 | 11/1967 | Knox et al. | 604/143 |
| 3,400,716 | 9/1968 | Schultz | 604/184 |
| 3,729,032 | 4/1973 | Tischlinger et al. | 141/2 |
| 3,738,539 | 6/1973 | Beich | 222/341 |
| 3,952,919 | 4/1976 | Hansen et al. | 222/89 |
| 4,046,145 | 9/1977 | Choksi | 604/407 |
| 4,204,539 | 5/1980 | VanBrugge | 604/148 |
| 4,261,359 | 4/1981 | Chein | 604/184 |
| 4,311,174 | 1/1982 | Walsh, III | 141/383 |
| 4,530,695 | 7/1985 | Phillips et al. | 604/184 |
| 4,715,853 | 12/1987 | Prindle | 604/184 |

FOREIGN PATENT DOCUMENTS 933101  6/1982  U.S.S.R. .

Primary Examiner—Samuel Scott
Assistant Examiner—Allen J. Flanigan
Attorney, Agent, or Firm—Ian C. McLeod

[57] ABSTRACT

A reusable syringe assembly (10) in combination with a disposable syringe assembly 11 is described. A plunger 11b of the disposable syringe assembly moves with a liquid (100) as a chamber (14) in the reusable syringe assembly is refilled, thereby eliminating a conventional vertical bottle connected to the reusable syringe assembly.

19 Claims, 2 Drawing Sheets

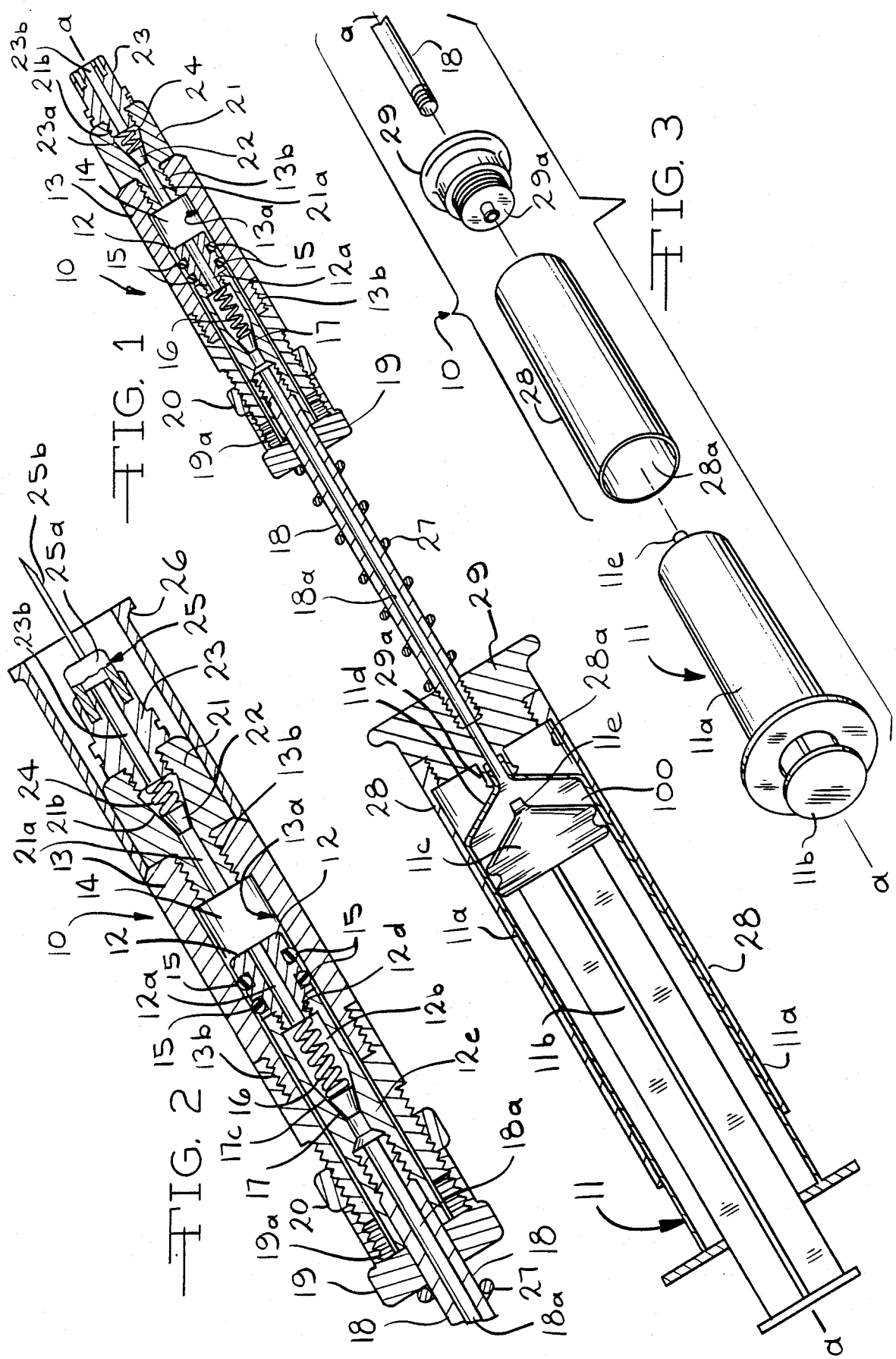

BACK-FILL SYRINGE

Cross-Reference to Related Application

This application is a continuation-in-part of Ser. No. 909,481, filed Sept. 19, 1986 now U.S. Pat. No. 4,715,853.

BACKGROUND OF THE INVENTION (1) Summary of the Invention

The present invention relates to an improved reusable syringe which on the plunging stroke of a piston injects a liquid through a needle into an animal and which refills with the liquid upon retraction of the piston from a supply means and referred to herein as a "back-fill syringe". In particular, the present invention relates to a reusable syringe which is filled at an end opposite the needle from a disposable syringe mounted in a handle of the reusable syringe used to inject the liquid from the reusable syringe.

(2) Prior Art

In the prior art, the supply means for the syringe is a bottle or other container with an opening to the outside which allows air to move into the container as the fluid is dispensed. This prevents a vacuum inside the container. U.S. Pat. No. 2,374,368 to Mejia discloses a valved reusable syringe with an open supply reservoir. U.S. Pat. Nos. 1,995,971 to Dowling and 3,353,537 to Knox et al describe two valve reusable syringes. U.S. Pat. No. 4,204,539 to Brugge discloses a hand operated reusable syringe with two valves. Other reusable syringes or injection devices are disclosed in U.S. Pat. Nos. 2,645,224 to Beebe; 2,757,670 to Ogle; 2,821,193 to Ziherl; 2,821,195 to McLintock; 3,400,716 to Schultz; 3,738,539 to Beich; 4,261,359 to Chein and 4,530,695 to Phillips.

Another syringe apparatus is described in Russian Pat. No. 933,101 to Timoshin. This patent describes a single-hand operated veterinary instrument for injecting livestock which incorporates systems for automatic sterilization of the injection needle and for disinfection and marking of the injected area with a colored disinfectant solution. A syringe, injection needle holder and ejector, and a bellows operated pump are mounted on a pistol-type grip body. The inlet of the syringe is connected by plastic tubing and a two-way valve to a bottle of veterinary preparation. The outlet is connected by plastic tubing and a sleeve to the injection needle. The inlet of the bellows is connected by plastic tubing to a bottle of colored disinfectant solution. The outlet is connected by plastic tubing and a sleeve to a spray on the injection needle holder. The ejector comprises a spring loaded striker which is activated by a trigger lever, the length of travel being controlled by stops. This device is complicated and has external hoses across the pistol grip body of the syringe which can easily become detached or damaged.

None of these prior art patents describe a reusable syringe which is mated to a disposable syringe so that the use of a tube connected to reservoir or a bottle mounted on the syringe can be avoided. There is a need for a compact, inexpensive, simple hand held device.

OBJECTS

It is therefore an object of the present invention to provide an improved back-fill reusable syringe apparatus supplied with fluid from a disposable syringe which has few moving parts and no exposed hoses or bottles and which is closed to the atmosphere outside of the syringe. Further it is an object of the present invention to provide a syringe apparatus which is reliable as well as relatively simple and inexpensive to construct. These and other objects will become increasingly apparent by reference to the following description and the drawings.

IN THE DRAWINGS

FIG. 1 is a front cross-sectional view illustrating an improved back-fill syringe 10 supplied by a liquid from a disposible syringe 11.

FIG. 2 is an enlarged partial sectional view of the syringe 10 of FIG. 1 showing the valve bodies 17 and 22 which control fluid flow through the piston 12 and out the needle 25.

FIG. 3 is a partial separated perspective view of the disposable syringe 11 and the handle 28 with a cylindrical opening 28a for mounting the disposable syringe 11.

FIG. 4 is a separated partial perspective view showing the syringe 10 of FIG. 1 and is a continuation of FIG. 3.

GENERAL DESCRIPTION

The present invention relates to a reusable syringe assembly for connection to a supply means which reloads a liquid to be dispensed by the syringe assembly after injecting a dose of the liquid into an animal which comprises: a piston means movable along a longitudinal axis for dispensing the liquid from the syringe assembly and which has an opening along the axis; a sleeve means confining the piston means for movement along the longitudinal axis and defining a chamber with the piston means for holding a liquid prior to dispensing, the sleeve means having a dispensing end with an opening for discharging the liquid and a charging end for receiving the liquid; tubular means connected at one end to the piston means along the longitudinal axis and extending from the charging end of the sleeve means to provide movement of the piston means in the sleeve means and to provide a fluid connection to the opening in the piston means, wherein the tubular means is to be connected to the supply means for the liquid; handle means grippable by one hand mounted on the tubular means away from the charging end of the sleeve means such that the tubular means can be moved to push the piston means in the sleeve means along the longitudinal axis by the hand on the handle means, wherein the handle means includes an elongate cylindrical opening inside the handle means with a conduit leading into the tubular means wherein the cylindrical opening is adapted to receive a disposable syringe assembly with a plunger as the supply means and a nozzle projecting into the conduit leading to the tubular means so as to provide the liquid in the reusable syringe assembly as the liquid is dispensed; and one-way valve means in the dispensing end of the sleeve means and the opening in the piston means or in the tubular means, whereby liquid can be dispensed from the chamber through the dispensing end of the sleeve means by the piston means with the valve means in the dispensing end open and with the valve means in the piston means or tubular means closed and whereby the chamber is refilled from the supply means by closing of the valve means in the dispensing end and by opening of the valve means in the piston means or tubular means.

Further the present invention relates to a reusable syringe assembly which reloads a liquid to be dispensed by the reusable syringe assembly from a supply means after injecting a dose of the liquid into an animal which comprises: a piston means movable along a longitudinal axis for dispensing the liquid from the syringe assembly and which has an opening along the axis; a sleeve means confining the piston means for movement along the longitudinal axis and defining a chamber with the piston means for holding the liquid prior to dispensing, the sleeve means having a dispensing end with an opening for discharging the liquid through a needle means to be mounted on the dispensing end and a charging end for receiving the liquid; tubular means connected at one end to the piston means along the longitudinal axis and extending from the charging end of the sleeve means to provide movement of the piston means in the sleeve means and to provide a fluid connection to the opening in the piston means wherein the tubular means is to be connected to a supply means for the liquid; handle means grippable by one hand mounted on the tubular means away from the charging end of the sleeve means such that the tubular means can be moved to push the piston means in the sleeve means along the longitudinal axis by the hand on the handle means, wherein the handle means includes an elongate cylindrical opening inside the handle means with a conduit leading into the tubular means, wherein the cylindrical opening is adapted to receive a disposable syringe assembly with a plunger as the supply means and with a nozzle projecting into the conduit leading to the tubular means, wherein the disposable syringe is adapted to contain a fluid to be dispensed so as to provide the liquid in the reusable syringe as the liquid is dispensed; and one-way valve means in the dispensing end of the sleeve means and the opening in the piston means or in the tubular means, whereby the liquid can be dispensed from the chamber through the dispensing end of the sleeve means by the piston means with the valve means in the dispensing end open and with the valve means in the tubular means or piston means closed when the needle means is inserted into the animal and the fluid injected by pushing the handle means along the longitudinal axis and whereby the chamber is refilled from the disposable syringe assembly means by closing of the valve means in the dispensing end and by opening of the valve means in the piston means.

Finally the present invention relates to a method for dispensing a liquid from a reusable syringe assembly which reloads a liquid to be dispensed by the reusable syringe assembly after injecting a dose of the liquid into an animal which comprises: a piston means movable along a longitudinal axis for dispensing the liquid from the syringe assembly and which has an opening along the axis; a sleeve means confining the piston means for movement along the longitudinal axis and defining a chamber with the piston means for holding the liquid prior to dispensing, the sleeve means having a dispensing end with an opening for discharging the liquid through a needle means to be mounted on the dispensing end and a charging end for receiving the liquid; tubular means connected at one end to the piston means along the longitudinal axis and extending from the charging end of the sleeve means to provide movement of the piston means in the sleeve means and to provide a fluid connection to the opening in the piston means wherein the tubular means is to be connected to a supply means for the liquid; handle means grippable by one hand mounted on the tubular means away from the charging end of the sleeve means such that the tubular means can be moved to push the piston means in the sleeve means along the longitudinal axis by the hand on the handle means wherein the handle means includes an elongate cylindrical opening inside the handle means with a conduit leading into the tubular means wherein the cylindrical opening is adapted to receive a disposable syringe assembly with a plunger as the supply means and with a nozzle projecting into the conduit leading to the tubular means wherein the disposable syringe is adapted to contain a fluid to be dispensed so as to provide the liquid in the reusable syringe as the liquid is dispensed; and one-way valve means in the dispensing end of the sleeve means and the opening in the piston means or in the tubular means, whereby the liquid can be dispensed from the chamber through the dispensing end of the sleeve means by the piston means with the valve means in the dispensing end open and with the valve means in the tubular means or piston means closed when the needle means is inserted into the animal and the fluid injected by pushing the handle means along the longitudinal axis and whereby the chamber is refilled from the disposable syringe assembly means by closing of the valve means in the dispensing end and by opening of the valve means in the piston means; dispensing the liquid by pushing the syringe assembly against the animal; and returning the piston means in the sleeve means to refill the chamber from the disposable syringe assembly, wherein the plunger in the disposable syringe assembly moves into the disposable syringe assembly as the fluid is dispensed.

SPECIFIC DESCRIPTION

FIGS. 1 to 4 show the reusable back-fill syringe assembly 10 of the present invention connected to a disposable syringe 11. The reusable syringe assembly 10 includes a piston 12 mounted on longitudinal axis a-a surround by a cylindrical wall 13a in a sleeve or housing 13. As shown in FIGS. 1 and 2, a chamber 14 is defined by the piston 12 and the housing 13. O-rings 15 are provided around the piston 12 and engage the cylindrical wall 13a of the housing 13. The housing 13 includes threaded connection part 13b which allows assembly of the housing 13 and piston 12. The piston 12 is provided with a hollow bore 12a around the longitudinal axis a-a which has an enlarged portion 12b supporting a spring 16 extending in a direction away from the chamber 14. The spring 16 engages a conically shaped one-way valve body 17 and urges the valve body 17 into a conically shaped recess 12c (FIG. 1) in piston 12 along the axis a-a. The tubular extension 12e from piston 12 has internal threads 12d to allow mounting of the valve body 17 inside the piston 12 and extension 12e. The piston 12 has a threaded portion 12f. A tubular member 18 is slideably mounted in a journal member 19 threaded on housing 13 and extends away from the housing 13. The tubular member 18 has a bore 18a throughout its length along axis a-a. The journal member 19 threads onto the housing 13. The journal member 19 has an extension 19a which engages a knurled nut 20 which locks the journal member 19 on housing 13 after the journal member 19 is positioned on the housing 13. The journal member 19 is moved on the housing 13 to move the piston 13 further into or out of the chamber 14 to thereby change the size of the chamber 14.

At the forward end of the syringe 11, a threaded opening 13b is connected to a second housing 21 with a first discharge opening 21a leading to a conically shaped one way tapered valve body 22 lodged in a tapered seat 21b in the opening 21a. A needle holder 23, which has a conventional needle lever lock (not shown), is mounted on the housing 21 and supports a coil spring 24 and has a second discharge opening 23b. The holder 23 supports conventional needle assembly 25 (FIG. 1) including a hub 25a and needle 25b extending from the holder 23. A shield 26 is provided around the needle assembly 25, holder 23 and second housing 21 to limit the penetration of the needle 25b into an animal.

At the rear of the syringe 11, a coil spring 27 is provided around the outside of the tubular member 18 with one end mounted through the journal member 19 and with the other end engaging a hollow handle 28 with a cylindrical opening 28a inside along axis a-a (FIG. 3).

The disposable syringe 11 is mounted in the opening 28a in handle 28 and includes a cylindrical outer member 11a confining a plunger 11b having a piston 11c (FIG. 1) conforming in shape to a front portion 11d of the outer member 11a. A nozzle 11e projects from the disposable syringe 11 into an opening in a receiver 29a on end plate 29 which is threaded into tubular member 28. The nozzle 11e is in sealed engagement with the receiver 29a. The end plate 29 supports the spring 28. A fluid 100 to be dispensed is provided inside the disposable syringe (FIG. 1).

Thus as can be seen from FIGS. 1 to 4, the plunger 11b of the disposable syringe 11 with the liquid 100 is inserted into opening 28a of handle 28 so that nozzle 11e sealingly engages receiver 29a. The plunger 11b is then pressed to fill the reusable syringe assembly 10 with the liquid 100. The animal is then injected by forcing needle 25b into the hide while shield 26 engages the hide thus dispensing the dose of liquid in chamber 14. During injection, the valve 17 is closed to prevent back flow of the liquid and the valve 22 is open. After insertion and removal of the needle from the hide of the animal, the spring 18 automatically retracts the piston 12 in housing 13 and the liquid refills the chamber 14, since valve 22 remains closed but valve 17 opens. The plunger 11b follows the liquid 100 as it is removed and prevents air from entering into the disposable syringe 11 or the reusable syringe 10.

The position of the valve bodies 17 and 22 in dispensing and filling from the chamber 14 is as follows in Table I.

TABLE I

| Dispensing from Chamber 14 | |
|---|---|
| Valve Body | Open or Closed |
| 17 | Closed |
| 22 | Open |
| Filling Chamber 14 | |
| 22 | Closed |
| 17 | Open |

As can be seen from the foregoing description, the one-way valve bodies 17 and 22 are preferably conical as are the corresponding seats 12c and 21b. Most preferably the valve bodies 17 and 22 are made of rubber to insure a complete seal. Other types of one-way valve means, such as balls which engage semi-circular seats, can be used as is well known to those skilled in the art. Preferably coil spring means such as springs 16 and 24 are used to urge the valve bodies 17 and 22 into the seats 12c and 21b since this allows liquid to pass through the spring and allows ease of disassembly and cleaning.

Preferably the piston 12 and housing 13 are cylindrical in cross-section as shown in FIG. 4. This allows ease of construction of the syringe assembly 10. The housing 13 and journal member 19 can be constructed of clear plastic to allow visual inspection of the chamber 14 and the inside of the syringe assembly 10.

Preferably spring 27 is used to retract the piston 12 in the housing 13 to refill the chamber 14. It will be appreciated that this can be done manually. Also, preferably the syringe chamber 14 has a volume of __cc or __cc.

Numerous variations will occur to those skilled in the art. It is intended that the foregoing description be only illustrative of the present invention and that this invention be limited only to the hereinafter appended claims.

I claim:

1. A reusable syringe assembly for connection to a supply means which reloads a liquid to be dispensed by the syringe assembly after injecting a dose of the liquid which comprises:

(a) a piston means movable along a longitudinal axis for dispensing the liquid from the syringe assembly and which has an opening along the axis;

(b) a sleeve means confining the piston means for movement along the longitudinal axis and defining a chamber with the piston means for holding a liquid prior to dispensing, the sleeve means having a dispensing end with an opening for discharging the liquid and a charging end for receiving the liquid;

(c) tubular means connected at one end to the piston means along the longitudinal axis and extending from the charging end of the sleeve means to provide movement of the piston means in the sleeve means and to provide a fluid connection to the opening in the piston means, wherein the tubular means is to be connected to the supply means for the liquid;

(d) handle means grippable by one hand mounted on the tubular means away from the charging end of the sleeve means such that the tubular means can be moved to push the piston means in the sleeve means along the longitudinal axis by the hand on the handle means, wherein the handle means includes an elongate cylindrical opening inside the handle means with a conduit leading into the tubular means, wherein the cylindrical opening is adapted to receive a disposable syringe assembly with a plunger as the supply means and a nozzle projecting into the conduit leading to the tubular means so as to provide the liquid in the reusable syringe assembly as the liquid is dispensed; and (e) one-way valve means in the dispensing end of the sleeve means and the opening in the piston means or in the tubular means, whereby liquid can be dispensed from the chamber through the dispensing end of the sleeve means by the piston means with the valve means in the dispensing end open and with the valve means in the piston means or tubular means closed and whereby the chamber is refilled from the supply means by closing of the valve means in the dispensing end and by opening of the valve means in the piston means or tubular means.

2. The apparatus of claim 1 wherein a return means is mounted on the assembly so as to move the piston means in the sleeve means back to the position for holding the liquid prior to dispensing and thus refill the chamber.

3. The syringe assembly of claim 2 wherein a coil spring means is provided as the return means around the tubular means between the sleeve means and the handle means to automatically retract the piston means in the sleeve means after the liquid is dispensed from the chamber.

4. The syringe assembly of claim 3 wherein each of the one-way valve means has a conical seat and a valve body which is conical and wherein each valve body is urged into a resting closed position by a valve coil spring which engages the valve body.

5. The syringe assembly of claim 1 wherein the tubular means slides in a journal member mounted on the sleeve means with a threaded nut on the sleeve means which abuts on the journal member to lock the journal member in position and wherein the journal member limits movement of the piston means in the sleeve means when chamber is refilled to thereby select the amount of fluids to be dispensed from the chamber.

6. The syringe assembly of claim 1 wherein the sleeve means comprises a cylindrical housing supporting the piston means and with a threaded journal member mounting the tubular means so that the journal member is threaded on the cylindrical housing to change the size of the chamber by limiting the movement of the piston means in the housing when the chamber is refilled and wherein a threaded nut is provided on the housing which locks the threaded journal member in position.

7. The syringe assembly of claim 1 wherein the disposable syringe has a friction fit with the cylindrical opening in the handle means.

8. A reusable syringe assembly which reloads a liquid to be dispensed by the reusable syringe assembly from a supply means after injecting a dose of the liquid into an animal which comprises:

(a) a piston means movable along a longitudinal axis for dispensing the liquid from the syringe assembly and which has an opening along the axis;

(b) a sleeve means confining the piston means for movement along the longitudinal axis and defining a chamber with the piston means for holding the liquid prior to dispensing, the sleeve means having a dispensing end with an opening for discharging the liquid through a needle means to be mounted on the dispensing end and a charging end for receiving the liquid;

(c) tubular means connected at one end to the piston means along the longitudinal axis and extending from the charging end of the sleeve means to provide movement of the piston means in the sleeve means and to provide a fluid connection to the opening in the piston means wherein the tubular means is to be connected to a supply means for the liquid;

(d) handle means grippable by one hand mounted on the tubular means away from the charging end of the sleeve means such that the tubular means can be moved to push the piston means in the sleeve means along the longitudinal axis by the hand on the handle means, wherein the handle means includes an elongate cylindrical opening inside the handle means with a conduit leading into the tubular means, wherein the cylindrical opening is adapted to receive a disposable syringe assembly with a plunger as the supply means and with a nozzle projecting into the conduit leading to the tubular means, wherein the disposable syringe is adapted to contain a fluid to be dispensed so as to provide the liquid in the reusable syringe as the liquid is dispensed; and (e) one-way valve means in the dispensing end of the sleeve means and the opening in the piston means or in the tubular means, whereby the liquid can be dispensed from the chamber through the dispensing end of the sleeve means by the piston means with the valve means in the dispensing end open and with the valve means in the tubular means or piston means closed when the needle means is inserted into the animal and the fluid injected by pushing the handle means along the longitudinal axis and whereby the chamber is refilled from the disposable syringe assembly means by closing of the valve means in the dispensing end and by opening of the valve means in the piston means.

9. The apparatus of claim 8 wherein a return means is mounted on the assembly so as to move the piston means in the sleeve means back to the position for holding the liquid prior to dispensing and thus to refill the chamber.

10. The syringe assembly of claim 9 wherein a coil spring means is provided as the return means around the tubular means between the sleeve means and the handle means to automatically retract the piston means in the sleeve means after the liquid is dispensed from the chamber.

11. The syringe assembly of claim 8 wherein a shield means is provided around the needle means on the dispensing end of the sleeve means with a portion of the needle means projecting along the axis outside the shield means so that the depth of penetration of the needle means into the animal is limited by the shield means.

12. The syringe assembly of claim 8 wherein each of the one-way valve means has a conical seat and a valve body which is conical and wherein each valve body is urged into a resting closed position by a coil spring which engages the valve body.

13. The syringe assembly of claim 8 wherein the valve means is in the piston means, wherein the valve means in the piston means and in the discharge end of the sleeve means each includes a valve coil spring urging a conically shaped valve body into a conical seat.

14. The syringe assembly of claim 8 wherein the tubular means slides in an adjustable threaded journal member mounted threadably on the sleeve means with a threaded nut on the sleeve means which abuts on the journal member to lock the journal member in position so that the journal member limits movement of the piston means in the sleeve means when the chamber is refilled to thereby select the amount of fluid to be dispensed from the chamber.

15. The syringe assembly of claim 8 wherein the sleeve means comprises a cylindrical housing supporting the piston means and with threaded journal member slideably mounting the tubular means so that the journal member is threaded on the cylindrical housing to change the size of the chamber by limiting the movement of the piston means in the housing when the chamber is refilled and wherein a threaded nut is provided on the housing which locks the threaded journal member in position.

16. The syringe assembly of claim 8 wherein the disposable syringe is adapted to have a friction fit with the cylindrical opening in the handle means.

17. A method for dispensing a liquid from a reusable syringe assembly which reloads a liquid to be dispensed by the reusable syringe assembly after injecting a dose of the liquid into an animal which comprises:

(a) a piston means movable along a longitudinal axis for dispensing the liquid from the syringe assembly and which has an opening along the axis;

a sleeve means confining the piston means for movement along the longitudinal axis and defining a chamber with the piston means for holding the liquid prior to dispensing, the sleeve means having a dispensing end with an opening for discharging the liquid through an needle means to be mounted on the dispensing end and a charging end for receiving the liquid;

tubular means connected at one end to the piston means along the longitudinal axis and extending from the charging end of the sleeve means to provide movement of the piston means in the sleeve means and to provide a fluid connection to the opening in the piston means wherein the tubular means is to be connected to a supply means for the liquid;

handle means grippable by one hand mounted on the tubular means away from the charging end of the sleeve means such that the tubular means can be moved to push the piston means in the sleeve means along the longitudinal axis by the hand on the handle means wherein the handle means includes an elongate cylindrical opening inside the handle means with a conduit leading into the tubular means wherein the cylindrical opening is adapted to receive a disposable syringe assembly with a plunger as the supply means and with a nozzle projecting into the conduit leading to the tubular means wherein the disposable syringe is adapted to contain a fluid to be dispensed so as to provide the liquid in the reusable syringe as the liquid is dispensed; and one-way valve means in the dispensing end of the sleeve means and the opening in the piston means or in the tubular means, whereby the liquid can be dispensed from the chamber through the dispensing end of the sleeve means by the piston means with the valve means in the dispensing end open and with the valve means in the tubular means or piston means closed when the needle means is inserted into the animal and the liquid injected by pushing the handle means along the longitudinal axis and whereby the chamber is refilled from the disposable syringe assembly means by closing of the valve means in the dispensing end and by opening of the valve means in the piston means;

(b) dispensing the liquid by pushing the syringe assembly against the animal; and (c) returning the piston means in the sleeve means to refill the chamber from the disposable syringe assembly, wherein the plunger in the disposable syringe assembly moves into the disposable syringe assembly as the fluid is dispensed.

18. The method of claim 17 wherein a return means is mounted on the assembly so as to move the piston means in the sleeve means back to the position for holding the liquid prior to dispensing and thus to refill the chamber.

19. The method of claim 17 wherein a coil spring means is provided as the return means around the tubular means between the sleeve means and the handle means to automatically retract the piston means in the sleeve means after the liquid is dispensed from the chamber.

* * * * *